United States Patent

Volodarsky et al.

Patent Number: 5,847,035
Date of Patent: Dec. 8, 1998

[54] SUBSTITUTEED TETRAHYDROPYRIMIDINE DERIVATIVES AND THEIR USE AS POLYMERIZATION INHIBITORS FOR VINYL AROMATIC COMPOUNDS

[75] Inventors: Leonid B. Volodarsky, Novosibirsk, Russian Federation; Vilen Kosover, Cheshire, Conn.

[73] Assignee: Uniroyal Chemical Company, Inc., Middlebury, Conn.

[21] Appl. No.: 816,630

[22] Filed: Mar. 13, 1997

[51] Int. Cl.$^6$ ............ C08K 5/3477; C07D 239/00; C07C 7/20

[52] U.S. Cl. ............ 524/100; 521/90; 521/128; 544/242; 560/4; 585/5

[58] Field of Search ............ 524/100; 585/5; 544/242; 560/4; 521/90, 128

[56] References Cited

U.S. PATENT DOCUMENTS

| | | | |
|---|---|---|---|
| 2,871,211 | 1/1959 | Mika | 544/242 |
| 3,408,422 | 10/1968 | May . | |
| 3,431,233 | 3/1969 | Murayama et al. . | |
| 3,432,578 | 3/1969 | Martin . | |
| 3,474,068 | 10/1969 | Murayama et al. | 544/242 |
| 3,513,170 | 5/1970 | Murayama et al. | 544/242 |
| 3,547,874 | 12/1970 | Murayama et al. . | |
| 3,644,278 | 2/1972 | Klemchuk . | |
| 3,733,326 | 5/1973 | Muryayama et al. . | |
| 3,899,491 | 8/1975 | Ramey et al. | 544/242 |
| 3,904,625 | 9/1975 | Alink . | |
| 3,926,994 | 12/1975 | White | 544/242 |
| 4,085,104 | 4/1978 | Alink . | |
| 4,145,545 | 3/1979 | Alink . | |
| 4,185,005 | 1/1980 | Thompson . | |
| 4,403,302 | 9/1983 | Gupta | 544/242 |
| 4,504,666 | 3/1985 | Earl et al. | 544/242 |
| 4,665,177 | 5/1987 | Rasshofer et al. | 544/242 |
| 4,665,185 | 5/1987 | Winter et al. . | |
| 4,761,414 | 8/1988 | Ellames et al. | 544/242 |
| 5,254,760 | 10/1993 | Winter et al. . | |
| 5,290,888 | 3/1994 | Gatechair et al. . | |

FOREIGN PATENT DOCUMENTS

| | | | |
|---|---|---|---|
| 2453174 | 5/1975 | Germany | 544/242 |
| 1027150 | 7/1983 | U.S.S.R. | 585/5 |
| WO 8304258 | 12/1983 | WIPO . | |

OTHER PUBLICATIONS

Brown et al., "From Carbonyl Compounds with Ammonia, Amines or Ureas" (11.2.2.), *The Pyrimidines,* 1993, p. 789; and list of references pp. 1294, 1354, and 1356.

Ma et al., "Oxoammonium Salts. 5.$^1$ A New Sythesis of Hindered Piperidines Leading to Unsymmetrical TEMPO–Type Nitroxides. Synthesis and Enantioselective Oxidations with Chiral Nitroxides and Chiral Oxoammonium Salts", *J. Org. Chem.,* 1993, 58, pp. 4837–4843.

*Primary Examiner*—Veronica P. Hoke
*Attorney, Agent, or Firm*—Raymond D. Thompson

[57] ABSTRACT

The present invention is directed to substituted tetrahydropyrimidine derivatives of the general formula

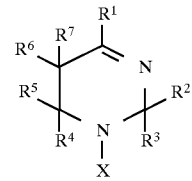

wherein $R^1$, $R^2$, $R^3$, $R^4$, $R^5$, $R^6$ and $R^7$, which may be the same or different, are hydrogen or alkyl aryl, cycloalkyl, alkaryl, aralkyl or heterocyclic, or substituted derivative thereof, $R^6$ or $R^7$ can additionally be —OH or —NR$^8$ wherein $R^8$ is hydrogen, alkyl, aryl, cycloalkyl, alkaryl, aralkyl or heterocyclic, or substituted derivative thereof, or $R^6$ and $R^7$ together can be =O or =NOH, and any two R groups on the same or adjacent carbon atoms can be joined in a cyclic configuration, and X is oxyl or hydroxy, it being provided that at least one of $R^2$ and $R^3$ and at least one of $R^4$ and $R^5$ are other than hydrogen.

30 Claims, No Drawings

SUBSTITUTEED TETRAHYDROPYRIMIDINE DERIVATIVES AND THEIR USE AS POLYMERIZATION INHIBITORS FOR VINYL AROMATIC COMPOUNDS

BACKGROUND OF THE INVENTION

This invention relates to substituted tetrahydropyrimidines and, in particular, the nitroxyl and hydroxy derivatives thereof, and the use of these derivatives as polymerization inhibitors for vinyl-containing and vinyl aromatic compounds and as polymer stabilizers.

Vinyl aromatic compounds such as styrene, the vinyl benzenes, the substituted styrenes and other vinyl group containing monomers and compounds have a pronounced tendency to undergo spontaneous polymerization during storage, shipping or processing as a result of an elevation in temperature and/or the random generation of free radicals. Since vinyl aromatic compounds produced by the usual industrial methods contain by-products and impurities, these compounds must be subjected to separation and purification processes in order to be suitable for further industrial applications. Such separation and purification is generally accomplished by distillation techniques. In order to inhibit or prevent polymerization of vinyl aromatic monomers during the distillation purification process or, for that matter, their premature polymerization at any time, various polymerization inhibitors for such monomers have been developed and/or proposed for use. Illustrative of known vinyl aromatic polymerization inhibitors are those described in, among others, U.S. Pat. Nos. 4,040,912; 4,252,615; 4,409,408; 4,457,806; 4,465,882; 4,654,451; 5,312,952; and, 5,540,861.

U.S. Pat. No. 5,254,760 discloses nitroxyl compounds useful as polymerization inhibitors for vinyl aromatic compounds such as styrene. The nitroxyl compounds conform to the general formula

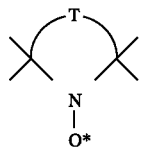

wherein each R is alkyl and T is a group required to complete a 5- or 6-membered ring. Specific nitroxyl compounds include 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, 1-oxyl-2,2,6,6-tetramethylpiperidin-4-yl acetate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate and 1-oxyl-2,2,6,6-tetramethy;piperidin-4-yl 4-tert-butyl-benzoate.

U.S. Pat. No. 4,665,185 discloses hydroxyl compounds useful as polymer stabilizers for polyolefins, polyesters, polyurethanes, and for conjugated diene polymers. The hydroxyl compounds conform to the general formula

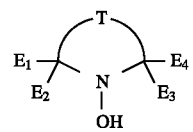

wherein $E_1$, $E_2$, $E_3$, and $E_4$ are independently an organic radical and T is a divalent group required to form a cyclic 5- or 6-membered ring. Specific hydroxyl compounds include di(1-hydroxy-2,2,6,6-tetramethylpiperoxidine-4-yl)sebacate and N-(1-hydroxy-2,2,6,6-tetramethylpiperidine-4-yl)-ε-caprolactam.

SUMMARY OF THE INVENTION

In accordance with the present invention, substituted tetrahydropyrimidine derivatives are provided having the general formula

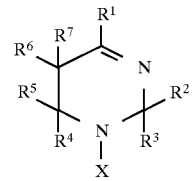

wherein $R^1$, $R^2$, $R^3$, $R^4$, $R^5$, $R^6$ and $R^7$, which may be the same or different, are hydrogen or alkyl, aryl, cycloalkyl, alkaryl, aralkyl or heterocyclic, or substituted derivative thereof, $R^6$ or $R^7$ can additionally be —OH or $NR^8$ where $R^8$ is hydrogen, alkyl, aryl, cycloalkyl, alkaryl, aralkyl or heterocyclic, or substituted derivative thereof, or $R^6$ and $R^7$ together can be =O or =NOH, and any two R groups on the same or adjacent carbon atoms can be joined in a cyclic configuration, and X is oxyl or hydroxy, it being provided that at least one of $R^2$ and $R^3$ and at least one of $R^4$ and $R^5$ is other than hydrogen, preferably $R^2$, $R^3$, $R^4$, $R^5$ are other than hydrogen.

While all of the substituted tetrahydropyrimidine compounds of this invention and their mixtures are useful as polymerization inhibitors for vinyl aromatic compounds such as styrene, those derivatives in which X is oxyl, i.e., the nitroxyl radical derivatives, are preferred for this use. The compounds in which X is hydroxy are also useful as stabilizers for polymers, e.g., polyolefins, polyethers, polyurethanes, etc.

DESCRIPTION OF THE PREFERRED EMBODIMENTS

The substituted tetrahydropyrimidine derivatives of this invention can be obtained by the oxidation of known substituted tetrahydropyrimidine compounds to provide the corresponding nitroxyls. The hydroxy derivatives can be obtained from the nitroxyls via reduction or directly from the 1,2,5,6-tetrahydropyrimidine compounds by oxidation. The starting substituted tetrahydropyrimidines and their preparation are disclosed in U.S. Pat. No. 4,085,104, the contents of which are incorporated by reference herein. These substituted tetrahydropyrimidine derivatives possess the general formula

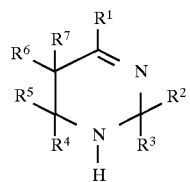

wherein $R^1$, $R^2$, $R^3$, $R^4$, $R^5$, $R^6$ and $R^7$ are the same as defined above.

Useful alkyls include methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, and the like, containing, e.g., up to about 25 carbon atoms, preferably no more than about 18 carbon atoms and more preferably no more than about 12 carbon atoms. Useful cyclohexyls include cyclopentyl, cyclohexyl, etc. and derivatives thereof such as alkylcyclohexyl, dialkylcyclohexyl, and the like.

Aryl, alkaryl and aralkyl include phenyl, alkylphenyl, polyalkylphenyl, chlorophenyl, alkoxyphenyl, naphthyl, alkylnaphthyl, benzyl, substituted benzyl, and the like. A preferred starting substituted tetrahydropyrimidine compound for making the nitroxyl and/or hydroxyl derivatives of this invention is 2,2,4,6,6-pentamethyl-1,2,5,6-tetrahydro-pyrimidine (acetonin).

The foregoing substituted tetrahydropyrimidines can be converted to the corresponding nitroxyl derivatives by catalytic oxidation employing, e.g., a hydroperoxide oxidizing agent as disclosed in U.S. Pat. No. 4,665,185, the contents of which are incorporated by reference herein. The nitroxyl derivatives can be reduced to provide the corresponding hydroxy derivatives. The reduction of the nitroxyl derivatives to the hydroxy derivatives can be accomplished by catalytic hydrogenation employing a noble metal or nickel catalyst or by a reduction using zinc, borane, hydrazine hydrate or other conventional reducing agent. If desired, the hydroxy derivatives can be converted to the corresponding nitroxyl derivatives employing a suitable oxidation procedure, e.g., the oxidation of the hydroxyl derivative with manganese oxide in ethyl acetate or ether.

The substituted tetrahydropyrimidine derivatives of this invention, and advantageously the nitroxyl derivatives, when employed as polymerization inhibitors for vinyl aromatic monomers can be introduced into the vinyl aromatic monomer to be protected by any conventional method. The inhibitor is generally introduced just upstream of the point of desired application by any suitable means, such as by the use of a proportionating pump. The polymerization inhibitor can be added as a concentrate but it is preferable to add it as a solution which is compatible with the monomer being treated. Suitable solvents include kerosene, naphtha, the lower alkanes such as hexane, aromatic solvents, such as toluene, alcohols, polyols or ketones, etc. It is often preferable to dissolve the inhibitor in the monomer to which the inhibitor is being added to avoid introducing additional impurities into the monomer. The concentration of polymerization inhibitor in the solvent is desirably in the range of about 1 to about 30 weight percent and preferably about 5 to about weight percent based on the total weight of inhibitor and solvent. The polymerization inhibitors herein are used at a concentration in the vinyl aromatic monomer which is effective to provide the desired protection against spontaneous polymerization. It has been determined that amounts of these derivatives in the range of from about 0.5 to about 1000 ppm based on the weight of the monomer being treated affords suitable protection against undesired polymerization. For most applications the inhibitor is used in amounts in the range of about 5 to about 500 ppm.

As previously noted, the hydroxy derivatives of this invention can be employed as stabilizers for polymers that are susceptible to degradation, e.g., deterioration due to oxidation, elevated temperature and/or exposure to light or other actinic radiation. The hydroxyl derivatives can be introduced into the polymer employing any known and conventional method. Examples of such polymers are poly-alpha-olefins such as polyethylene, polypropylene, polybutylene, and polyisoprene, copolymers of poly-alpha-olefins, polyamides, polyesters, polycarbonates, polyacetals, polystyrene, and conjugated diene polymers. Other polymers that can be stabilized by the hydroxyl derivatives of this invention include polyether polyols and polyurethane foams derived therefrom. The hydroxyl derivatives are added to the polymer in an amount sufficient to impart an appreciable stabilizing effect. In general, this amount may vary from about 0.1 to about 2 weight percent, preferably from about 0.2 to about 1 weight percent and more preferably from about 0.4 to about 0.6 weight percent by total weight of the polymer.

The following examples illustrate the process of preparing the compositions of this invention.

EXAMPLE 1

This example illustrates the preparation of 1-hydroxy-2,2,4,6,6-pentamethyl-1,2,5,6-tetrahydropyrimidine (1-hydroxy acetonin).

To a solution of sodium carbonate (1.2 g) or sodium bicarbonate (2.4 g), sodium tungstate (0.4 g), ethylenediaminetetraacetic acid (EDTA) (0.4 g), and 2,4,6,6-pentamethyl-1,2,5,6-tetrahydropyrimidine (acetonin; 4.62 g) in 50 ml water at 5° C. was added 35 weight percent hydrogen peroxide (7 ml) over 30 minutes, maintaining a temperature of about 5° C. The resulting mixture was stirred an additional 15 minutes at 5° C. and saturated with potassium carbonate or bicarbonate. The mixture was transferred to a separatory funnel and extracted with 4×20 mL diethylether. To the combined diethylether phases was added hydrazine hydrate (1 ml). The resulting mixture was stirred for 5 minutes. The solvent was evaporated under reduced pressure, giving 1.2 g (23.6% yield) of product 1-hydroxy-2,2,4,6,6-pentamethyl-1,2,5,6-tetrahydropyrimidine (1-hydroxy acetonin).

EXAMPLE 2

This example illustrates the preparation of 1-oxyl-2,2,4,6,6-pentamethyl-1,2,5,6-tetrahydropyrimidine (1-oxyl acetonin).

To a solution of 1-hydroxy-2,2,4,6,6-pentamethyl-1,2,5,6-tetrahydropyrimidine (0.55 g) in diethylether (20 ml) was added manganese dioxide (0.5 g) at room temperature. The mixture was stirred at room temperature for 1 hour, filtered, and the filtrate evaporated under reduced pressure, giving 0.47 g (85.5% yield) of product 1-oxyl-2,2,4,6,6-pentamethyl-1,2,5,6-tetrahydropyrimidine (1-oxyl acetonin, or acetonin nitroxyl radical) as a red oil.

EXAMPLE 3

This example illustrates the polymerization inhibitory effectiveness of the 1-hydroxy acetonin of Example 1 and the 1-oxyl acetonin of Example 2 in commercial grade styrene.

To a 3-neck, 50 ml round bottom flask fitted with a thermometer, a reflux condenser whose top opening is capped with a septum through which an 18-gauge syringe needle has been inserted, a gas inlet tube, and a magnetic stirrer, was added 40 g of the inhibitor/styrene solution. The stirred sample was prepurged with a subsurface flow of argon at 10 cc/minute for fifteen minutes. The flask was then immersed in an oil bath, and the temperature of the styrene solution was brought to and maintained at 118°±0.2° C., maintaining a 5 cc/minute subsurface flow of argon. Samples were removed periodically, and the polystyrene content was determined by refractive index measurements, calibrated with authentic polystyrene in styrene solutions of known concentration. The induction time was the amount of time required to make 1.00 weight percent polystyrene. (Time equals zero when the styrene solution reaches 118° C.) Thus, the longer the induction time, the greater the inhibiting ability of the material.

| Inhibitor | Concentration (ppm) | Induction Time (minutes) |
|---|---|---|
| 1-hydroxy acetonin | 100 | 28 |
| 1-oxyl acetonin | 100 | 43 |
| no inhibitor | — | 5 |

As these data show, the presence of 1-hydroxy acetonin and 1-oxyl acetonin in the styrene monomer samples resulted in a significant increase in the induction time for polymerization to occur relative to that for the styrene monomer sample containing no polymerization inhibitor.

EXAMPLE 4

This example illustrates the preparation of 1-oxyl-2,2,4,6,6-pentamethyl-1,2,5,6-tetrahydropyrimidine (acetonin nitroxyl).

A reaction flask employed with a magnetic stirrer was charged with a solution of water containing 1.2 g (0.03 mole) sodium hydroxide, 4.6 g (0.03 mole) acetonin, 0.4 g $Na_2WO_4$ and 0.4 g EDTA. 7 ml of hydrogen peroxide 30% was added in three portions at a temperature of 25° C. while efficiently stirring the clear solution. The temperature of the solution was increased to 35° C. giving an exothermic reaction with the temperature being further increased to 55° C. over a 10 to 20 minute period. The clear solution then turned to bright orange.

The temperature of the solution was decreased to ambient temperature. The solution was then saturated with potassium bicarbonate and extracted with ether three times with 20 ml ether used in each extraction. The combined ether extracts were dried over anhydrous magnesium sulfate and evaporated. Gas chromatography showed 4 g of residue oil contained about 50% acetonin nitroxyl.

EXAMPLE 5

This example illustrates the preparation of 1-hydroxy-2,2,4,6,6-pentamethyl-1,2,5,6-tetrahydropyrimidine (1-hydroxy acetonin).

To the one half of dried ether solution prepared using the method of Example 4, 1 ml of hydrazine was added. When the ether extracts were evaporated, the bright orange color became clear and a white precipitate formed. 0.9 g of the white precipitate was recrystallized from ethyl acetate giving 0.7 g of product 1-hydroxy-2,2,4,6,6-pentamethyl-1,2,5,6-tetrahydropyrimidine (1-hydroxy acetonin) having a melting point of 142°–144° C.

EXAMPLE 6

This example illustrates the preparation of 1-oxyl-2,2,4,6,6-pentamethyl-1,2,5,6-tetrahydropyrimidine (acetonin nitroxyl).

A mixture of solution containing 1.2 g NaOH, 0.4 g $Na_2WO_4$ and 0.4 g EDTA in 20 ml water and 4.6 g acetonin in 20 ml $CH_3OH$ was cooled to 5° C. 7 ml of hydrogen peroxide 30% was then added to this mixture in one portion with the temperature and color of the solution remaining unchanged. The temperature of the reaction mixture was increased to 35°–40° C. giving an exothermic reaction that continued for a period of 10 to 15 minutes with the temperature being further increased to 50°–55° C. The clear solution turned to bright orange. The methanol was evaporated in vacuum. The water solution was processed according to the same method provided in Example 4 producing 4 g of the same residue oil. Gas chromatography showed the 4 g of residue oil contained about 50% acetonin nitroxyl (45–50% yield).

EXAMPLE 7

This example illustrates the preparation of 1-hydroxy-2,2,4,6,6-pentamethyl-1,2,5,6-tetrahydropyrimidine (1-hydroxy acetonin).

Ammonia from a balloon was bubbled into 60 ml (1.0 mole) acetone containing 0.4 g (0.004 mole) NaBr and 0.3 g (0.004 mole) $NH_4SCN$ for 5 hours. During the first hour, the reaction mixture was cooled in an ice bath and then the temperature was increased to ambient. The mixture was stirred for two hours and mixed with 30 ml of 50% aqueous NaOH.

The organic layer was separated with the unreacted acetone being evaporated under vacuum at a temperature below 35° C. The thick viscous residue product was solidified in the freezer into ample crystal mass. This mass was quickly filtered and rinsed with a small amount of cooled ether producing 38 g (60% yield) of acetonin monohydrate in the form of white crystals. 3.8 g (0.022 mole) acetonin monohydrate in the same condition as Example 4 produced about 3 g of an orange oil containing 54.7% acetonin nitroxyl and 1.5% 1-hydroxy acetonin according to gas chromatography. 1.5 g of the oil was reduced by hydrazine using the same process as Example 5 giving 0.9 g 1-hydroxy acetonin.

EXAMPLE 8

This example illustrates the preparation of 1-oxyl-2,2,4,6,6-pentamethyl-1,2,5,6-tetrahydropyrimidine (acetonin nitroxyl).

0.6 g of fresh recrystallized 1-hydroxy-acetonin was stirred with 0.6 g manganese oxide in 20 ml of ether over a two hour period at ambient temperature. The red colored ether solution was filtered from manganese oxide and evaporated. 0.55 g of a residue red oil was pure acetonin nitroxyl with a yield of 99% according to gas chroma-tography. The residue oil was crystallized in the form of red low melting crystals in a freezer.

What is claimed is:

1. A substituted tetrahydropyrimidine compound of the general formula

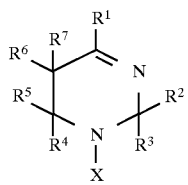

wherein $R^1$, $R^2$, $R^3$, $R^4$, $R^5$, $R^6$, and $R^7$, which may be the same or different, are hydrogen or alkyl, aryl, cycloalkyl, alkaryl, aralkyl, substituted derivative thereof, $R^6$ or $R^7$ can additionally be —OH or —$NR^8$ wherein $R^8$ is hydrogen, alkyl, aryl, cycloalkyl, alkaryl or aralkyl, or substituted derivative thereof, and X is oxyl or hydroxy, it being provided that at least one of $R^2$ and $R^3$ and at least one of $R^4$ and $R^5$ are other than hydrogen.

2. The compound of claim 1 wherein $R^1$, $R^6$ and $R^7$ are hydrogen and at least one of $R^2$ and $R^3$ and at least one of $R^4$ and $R^5$ are alkyl of from 1 to about 25 carbon atoms.

3. The compound of claim 1 wherein $R^1$, $R^6$ and $R^7$ are hydrogen, at least one of $R^2$ and $R^3$ and at least one of $R^4$ and $R^5$ are alkyl of from 1 to about 25 carbon atoms and X is oxyl.

4. The compound of claim 1 wherein $R^1$, $R^6$ and $R^7$ are hydrogen, at least one of $R^2$ and $R^3$ and at least one of $R^4$ and $R^5$ are alkyl of from 1 to about 25 carbon atoms and X is hydroxy.

5. The compound of claim 1 wherein $R^1$, $R^6$ and $R^7$ are hydrogen and at least one of $R^2$ and $R^3$ and at least one of $R^4$ and $R^5$ are methyl.

6. The compound of claim 1 wherein $R^1$, $R^6$ and $R^7$ are hydrogen, at least one of $R^2$ and $R^3$ and at least one of $R^4$ and $R^5$ are methyl and X is oxyl.

7. The compound of claim 1 wherein $R^1$, $R^6$ and $R^7$ are hydrogen, at least one of $R^2$ and $R^3$ and at least one of $R^4$ and $R^5$ are methyl and X is hydroxy.

8. The compound of claim 1 wherein X is oxyl.

9. The compound of claim 1 wherein X is hydroxy.

10. The compound of claim 1 which is 1-oxyl-2,2,4,6,6-pentamethyl-1,2,5,6-tetrahydropyrimidine.

11. The compound of claim 1 which is 1-hydroxy-2,2,4,6,6-pentamethyl-1,2,5,6-tetrahydropyrimidine.

12. A vinyl containing composition comprising at least one vinyl group containing compound and a polymerization inhibitory effective amount of at least one substituted tetrahydro-pyrimidine derivative of the general formula

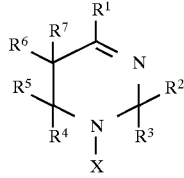

wherein $R^1$, $R^2$, $R^3$, $R^4$, $R^5$, $R^6$, and $R^7$, which may be the same or different, are hydrogen or alkyl, aryl, cycloalkyl, alkaryl, aralkyl, or substituted derivative thereof, $R^6$ or $R^7$ can additionally be —OH or —$NR^8$ wherein $R^8$ is hydrogen, alkyl, aryl, cycloalkyl, alkaryl or aralkyl, or substituted derivative thereof, and X is oxyl or hydroxy, it being provided that at least one of $R^2$ and $R^3$ and at least one of $R^4$ and $R^5$ are other than hydrogen.

13. The composition of claim 12 wherein X is oxyl.

14. The composition of claim 13 wherein the vinyl containing compound is a vinyl aromatic compound selected from the group consisting styrene, ethylbenzene, vinyl benzenes and substituted styrenes.

15. The composition of claim 13 wherein in the substituted tetrahydropyrimidine derivative, $R^1$, $R^6$ and $R^7$ are hydrogen and at least one of $R^2$ and $R^3$ and at least one of $R^4$ and $R^5$ are alkyl of from 1 to about 25 carbon atoms.

16. The composition of claim 13 wherein in the substituted tetrahydropyrimidine, $R^1$, $R^6$ and $R^7$ are hydrogen and at least one of $R^2$ and $R^3$ and at least one of $R^4$ and $R^5$ are methyl.

17. The composition of claim 13 wherein the substituted tetrahydropyrimidine is 1-oxyl-2,2,4,6,6-pentamethyl-1,2,5,6-tetrahydropyrimidine.

18. The composition of claim 13 wherein the substituted tetrahydropyrimidine is 1-hydroxy-2,2,4,6,6-pentamethyl-1,2,5,6-tetrahydropyrimidine.

19. A stabilized composition comprising at least one polymer which is susceptible to degradation and in need of stabilization to prevent or inhibit such degradation and a stabilizing effective amount of at least one substituted tetrahydropyrimidine derivative of the general formula

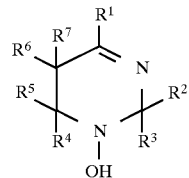

wherein $R^1$, $R^2$, $R^3$, $R^4$, $R^5$, $R^6$, and $R^7$, which may be the same or different, are hydrogen or alkyl, aryl, cycloalkyl, alkaryl, aralkyl, or substituted derivative thereof, $R^6$ or $R^7$ can additionally be —OH or —$NR^8$ wherein $R^8$ is hydrogen, alkyl, aryl, cycloalkyl, alkaryl or aralkyl, or substituted derivative thereof, it being provided that at least one of $R^2$ and $R^3$ and at least one of $R^4$ and $R^5$ are other than hydrogen.

20. The composition of claim 18 wherein the polymer which is susceptible to degradation is selected from the group consisting of polyolefins, polyesters, and polyurethanes.

21. The composition of claim 18 wherein in the substituted tetrahydropyrimidine derivative, $R^1$, $R^6$ and $R^7$ are hydrogen and at least one of $R^2$ and $R^3$ and at least one of $R^4$ and $R^5$ are alkyl of from 1 to about 25 carbon atoms.

22. The composition of claim 18 wherein in the substituted tetrahydropyrimidine, $R^1$, $R^6$ and $R^7$ are hydrogen and at least one of $R^2$ and $R^3$ and at least one of $R^4$ and $R^5$ are methyl.

23. The composition of claim 18 wherein the substituted tetrahydropyrimidine is 1-hydroxy-2,2,4,6,6-pentamethyl-1,2,5,6-tetrahydropyrimidine.

24. A method for inhibiting the polymerization of a vinyl aromatic compound which comprises adding thereto a polymerization inhibiting amount of at least one substituted tetrahydropyrimidine derivative of the general formula

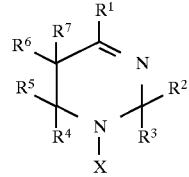

wherein $R^1$, $R^2$, $R^3$, $R^4$, $R^5$, $R^6$, and $R^7$, which may be the same or different, are hydrogen or alkyl, aryl, cycloalkyl, alkaryl, aralkyl, or substituted derivative thereof, $R^6$ or $R^7$ can additionally be —OH or —$NR^8$ wherein $R^8$ is hydrogen, alkyl, aryl, cycloalkyl, alkaryl or aralkyl, or substituted derivative thereof, and X is oxyl or hydroxy, it being provided that it least one of $R^2$ and $R^3$ and at least one of $R^4$ and $R^5$ are other than hydrogen.

25. The method of claim 23 wherein X is oxyl.

26. The method of claim 24 wherein the vinyl aromatic compound is styrene.

27. The method of claim 24 wherein the substituted tetrahydropyrimidine is 1-oxyl-2,2,4,6,6-pentamethyl-1,2,5,6-tetrahydropyrimidine.

28. A method for stabilizing at least one polymer which is susceptible to degradation and in need of stabilization to prevent or inhibit such degradation which comprises adding thereto a stabilizing effective amount of at least one substituted tetrahydropyrimidine derivative of the general formula wherein $R^1$, $R^2$, $R^3$, $R^4$, $R^5$, $R^6$, and $R^7$, which may be the same or different, are hydrogen or alkyl, aryl, cycloalkyl, alkaryl, aralkyl, or substituted derivative thereof, $R^6$ or $R^7$ can additionally be —OH or —$NR^8$ wherein $R^8$ is hydrogen, alkyl, aryl, cycloalkyl, alkaryl or aralkyl, or substituted derivative thereof, it being provided that at least one of $R^2$ and $R^3$ and at least one of $R^4$ and $R^5$ are other than hydrogen.

29. The method of claim 27 wherein the polymer which is susceptible to degradation is selected from the group consisting of polyolefins, polyesters, and polyurethanes.

30. The method of claim 27 wherein the substituted tetrahydropyrimidine is 1-hydroxy-2,2,4,6,6-pentamethyl-1,2,5,6-tetrahydropyrimidine.

* * * * *